US012608893B2

(12) United States Patent     (10) Patent No.:   US 12,608,893 B2

Tranchant et al.     (45) Date of Patent:     Apr. 21, 2026

(54) CONJUNCTION OF 2D AND 3D VISUALIZATIONS IN AUGMENTED REALITY

(71) Applicant: Brainlab SE, Munich (DE)

(72) Inventors: Florentin Tranchant, Munich (DE);
Oliver Fleig, Baldham (DE);
Maximilian Schindler, Munich (DE);
Falko Seifferth, Munich (DE)

(73) Assignee: BRAINLAB SE, Munich (DE)

( * ) Notice: Subject to any disclaimer, the term of this patent is extended or adjusted under 35 U.S.C. 154(b) by 142 days.

(21) Appl. No.: 18/579,729

(22) PCT Filed: Dec. 27, 2022

(86) PCT No.: PCT/EP2022/087878

§ 371 (c)(1),
(2) Date: Jan. 16, 2024

(87) PCT Pub. No.: WO2024/141152

PCT Pub. Date: Jul. 4, 2024

(65) Prior Publication Data

US 2025/0078418 A1     Mar. 6, 2025

(51) Int. Cl.
*G06T 19/00*     (2011.01)
*A61B 90/00*     (2016.01)
(52) U.S. Cl.
CPC ............ *G06T 19/006* (2013.01); *A61B 90/37* (2016.02); *A61B 2090/365* (2016.02)
(58) Field of Classification Search
CPC ......... A61B 34/25; A61B 90/37; A61B 34/20; A61B 2090/365; A61B 2017/00207;
A61B 2034/2068; A61B 2034/105; A61B 2090/372; A61B 2090/502; A61B 2034/2055; A61B 34/10; G06T 19/006; G06T 2210/41; G06T 19/20; G06T 17/00; G06T 19/00; G06V 2201/03; G06V 2201/034
See application file for complete search history.

(56) References Cited

U.S. PATENT DOCUMENTS

| | | | |
|---|---|---|---|
| 12,211,151 B1 * | 1/2025 | Chiou ................... | G06T 19/003 |
| 2011/0236868 A1 * | 9/2011 | Bronstein .............. | G09B 23/30 |
| | | | 434/267 |
| 2019/0254754 A1 | 8/2019 | Johnson | |
| 2020/0405395 A1 * | 12/2020 | Gullotti ............... | A61B 17/809 |
| 2022/0405935 A1 | 12/2022 | Flossmann | |

(Continued)

FOREIGN PATENT DOCUMENTS

WO     2022161610 A1     8/2022

OTHER PUBLICATIONS

International Searching Authority, Notification of Transmittal of the International Search Report and the Written Opinion issued in Application No. PCT/EP2022/087878, 13 pages, dated Jun. 20, 2023.

*Primary Examiner* — Xilin Guo
(74) *Attorney, Agent, or Firm* — Gray Ice Higdon

(57) ABSTRACT

The present invention relates to a method and a system for providing an augmentation (12) of a user's visual perception of the real world, that includes a display (13, 14, 15) of two-dimensional images in conjunction with three-dimensional virtual objects (17), which are displayed with respect to each other in a clear and easily understandable manner.

15 Claims, 6 Drawing Sheets

(56) References Cited

U.S. PATENT DOCUMENTS

| | | | |
|---|---|---|---|
| 2023/0240790 A1* | 8/2023 | Wiegel ................. | A61B 8/5253 |
| | | | 600/424 |
| 2023/0390021 A1* | 12/2023 | Polchin .................. | A61B 34/30 |
| 2024/0299100 A1* | 9/2024 | Minne ................... | A61B 90/20 |

* cited by examiner

CONJUNCTION OF 2D AND 3D VISUALIZATIONS IN AUGMENTED REALITY

FIELD OF THE INVENTION

The present invention relates to a computer-implemented method of providing an augmentation of a field of view via an augmented reality device, a corresponding computer program, a computer-readable storage medium storing such a program and a computer executing the program, as well as a medical system comprising an electronic data storage device and the aforementioned computer.

TECHNICAL BACKGROUND

In recent years the role of augmented reality (AR) has become increasingly important in the field of healthcare. With the help of augmented reality, digital information or content can be integrated into a user's visual perception of the real world and even allows for interacting with virtual objects placed in the real world. Insofar, augmented reality helps in surgery planning and patient treatment and improves the perception of complex medical situations, not only for patients but also for medical personnel including surgeons.

Prior art concepts of providing augmented reality in the medical filed are based on the insertion of virtual three-dimensional objects into the user's field of view, which may be registered, i.e. brought into positional alignment with their real-world counterparts. Other augmented reality concepts include virtual screens projected into the user's field of view, in which two-dimensional image information may be displayed to the user, thereby replacing actual monitors or computer screens.

The present invention has the object of providing an augmented reality concept for displaying two-dimensional image information along with three-dimensional virtual object information in a clear and easily understandable manner.

The present invention can be used for any medical procedures including the use of augmented reality e.g. in connection medical navigation systems such as Curve® or Kick®, both products of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The present invention relates to a method and a system for providing an augmentation of a user's visual perception of the real world, that includes a display of two-dimensional images in conjunction with three-dimensional virtual objects, which are displayed with respect to each other in a clear and easily understandable manner.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of providing an augmentation of a field of view via an augmented reality device. The method comprises executing, on at least one processor of at least one computer (for example at least one computer being part of a navigation system), the following exemplary steps which are executed by the at least one processor.

In a (for example first) exemplary step, image data is acquired which describes at least one slice image of the patient's anatomy registered with the patient's actual anatomy. For example, a three-dimensional image dataset may be acquired from which two-dimensional slice images can be reconstructed. The three-dimensional image dataset may be acquired via any conceivable volumetric imaging modality such as CT, MR and radiography imaging. The spatial location and/or orientation of reconstructed slice images within the three-dimensional image dataset may be, as will be described further below, defined on the basis of a spatial position and/or orientation of a movable object.

In a (for example second) exemplary step, movable object data is acquired which describes a spatial position of a movable object, particularly a handheld device or instrument, with respect to the patient's anatomy. As soon as the three-dimensional image dataset is registered, i.e. spatially aligned with the patient's actual anatomy, the spatial position and/or orientation of such movable object may be tracked with respect to the patient's actual anatomy and therefore also with respect to the three-dimensional image dataset. For determining and tracking the object's position and/or orientation over time may involve the use of a medical tracking system, for example an optical tracking system comprising one or more optical cameras monitoring the movable object and the patient's anatomy, particularly one or more tracking markers attached thereto.

In a (for example third) exemplary step, object of interest data is acquired which describes a model and a spatial position of at least one object of interest with respect to the patient's anatomy. In other words, a virtual representation of one or more objects of interest is determined and put into a spatial relation with the three-dimensional image dataset and the patient's actual anatomy registered thereto. For example, such objects of interest may include any objects that remain static with respect to the patient's anatomy, for example anatomical structures which may have been identified manually by a surgeon (e.g. by outlining the structure's contours in a visualization of the three-dimensional image dataset) or automatically via an anatomical atlas based segmentation of that structure within the three-dimensional image dataset. Moreover, any conceivable artificial structure may also represent an object of interest. For example, any implant (e.g. (pedicle-) screws or cages in spinal surgery, joint implants in hip or knee surgery) may be identified as objects of interest, the spatial position and/or orientation of which is determined once or even tracked over time with respect to the patient's anatomy and the three-dimensional image dataset. Moreover, even spatially tracked instruments such as tools or pointers held manually or with robotic assistance may represent objects of interest.

In a (for example fourth) exemplary step, augmentation data is determined based on the previously acquired image data, movable object data and object of interest data, wherein the augmentation data describes an augmentation of the field of view provided via the augmented reality device, including the at least one slice image and a three-dimensional representation of the at least one object of interest registered with the at least one slice image, wherein the sectional plane of the at least one slice image is defined based on the spatial position of the movable object. In other words, an augmented reality overlay to be injected into the user's field of view is calculated based on the previously acquired data.

First of all, the overlay includes a visual representation of the at least one slice image of the patient's anatomy which may be displayed via one or more two-dimensional screens. The slice image representation, particularly the virtual screen may be oriented along predefined directions, such as anatomical directions of the patient's anatomy and/or along directions defined by actual real-world objects within the surgical site. For example, the plane of the image representation or of the virtual screen may be spanned by a cranial-caudal direction of the patient's anatomy and a vertical direction, i.e. the gravitational vector at the surgical site. It is also conceivable that the plane of the image representation or of the virtual screen is inclined with respect to any of these directions by a defined amount. Further, the image representation or the virtual screen may be positioned at a predefined location within the user's field of view, but may also take a predefined position with respect to actual real-world objects within the user's field of view. For example, the image representation or the virtual screen may be positioned next to, for example above, the patient's anatomy, particularly a surgical site, but may also be positioned next to (e.g. left, right, above, below) a static or movable real-word object such as a patient table or hand-held instrument.

In this regard, it is important to note that the sectional plane of the at least one slice image shown in the image representation or on the virtual screen is defined by the position and/or orientation of the movable object (e.g. hand-held device or instrument) which appears as real-world object within the user's field of view. Thus, the position and/or the orientation of the sectional plane within the three-dimensional image dataset is changed as the position and/or orientation of the movable object is changed. Such change of the position and/or orientation of the movable object may be caused by a user grasping the object/instrument and moving it to a desired position and/or orientation. It is however also conceivable that the change in the object's position and/or orientation is caused by a medical robot adapted to manipulate the object/instrument.

Further, the augmented reality overlay comprises a three-dimensional visual representation of the at least one object of interest, which is registered, i.e. positionally aligned with the three-dimensional image dataset and is therefore displayed at a correct position and/or orientation with respect to the at least one slice image shown in the AR-overlay. In still other words, the AR-overlay comprises a combined, i.e. merged visualization of at least one two-dimensional anatomical slice image and a three-dimensional representation of at least one object of interest. Consequently, the shown objects of interest "protrude" from the plane of the virtual screens showing the anatomical slice images.

In an example of the method described herein, the at least one slice image of the patient's anatomy includes:
   at least one two-dimensional image of the patient's anatomy; and/or
   at least one planar, three-dimensional image volume having a limited slice-thickness, particularly with the sectional plane forming the centre plane of the image volume;
particularly wherein the at least one slice image is reconstructed from a three-dimensional image dataset of the patient's anatomy.

In other words, at least one of the virtual screens may show an exactly two-dimensional image of the patient's anatomy. However, it is also conceivable that at least one of the virtual screens shows a three-dimensional image volume having a shallow thickness in a direction perpendicular to the plane of the virtual screen. Thus, the corresponding screen shows, up to a predefined distance, the patient's anatomy in front of and behind the sectional plane of the corresponding slice image. As compared to the height and the width of the virtual screen, the shown depth may be comparatively small, for example 5%, 10% or 15% of the height and/or the width of the screen.

In a further example of the method described herein, the sectional plane of the at least one slice image is defined
   to include or to extend along a longitudinal axis of the movable object; or
   to extend perpendicularly with respect to the longitudinal axis of the movable object.

As was described further above, the at least one slice image's sectional plane changes its position and/or orientation with respect to the three-dimensional image dataset, i.e. within the coordinate system assigned to the three-dimensional image dataset in correspondence with the spatial position and/or orientation of the movable object tracked via the medical tracking system. Thus, a user is able to change the image content shown via the at least one virtual screen by moving the object with respect to the patient's anatomy. In a specific example, the movable object may be represented by a pointer instrument, wherein two virtual screens may show slice images the sectional planes of which contain the longitudinal pointer axis, and wherein the sectional planes are oriented perpendicularly to each other. Such slice images are herein referred to as "inline"-views. A third virtual screen may show a slice image the sectional plane of which extends perpendicularly with respect to the longitudinal pointer axis, which is herein to as "probe's eye"-view.

In a still further example of the method described herein, the sectional plane of the at least one slice image is defined, particularly is further defined to extend in an anatomical direction defined for the patient's anatomy, particularly in
   a cranial-caudal direction;
   a medial-lateral direction; or
   an anterior-posterior direction.

It is important to note that the plane of the image representation, i.e. of the virtual screen as displayed within the user's field of view may differ from the sectional plane of a slice image shown on this particular virtual screen. While the sectional plane is defined with respect to the patient's actual anatomy and the three-dimensional image dataset, i.e. defines the position and/or orientation of a reconstructed image within the coordinate system of the three-dimensional image dataset, the plane of the virtual screen refers to the positional orientation of the screen within the user's field of view and perceived by the user when looking at the surgical site.

Coming back to the sectional plane of the at least one slice image, the sectional plane may be spanned by a longitudinal axis of the movable object and one predefined, particularly anatomical direction as described above.

As already outlined further above, the at least one object of interest may be selected from the group comprising:
   permanent medical implants, particularly bone screws and bone nails;
   temporary medical implants, particularly electrodes and catheters;
   pathological anatomical structures, particularly tumors and lesions;

treatment volumes, particularly radiation dose distribu-
tions, particle radiation fields and electromagnetic
radiation fields;
anatomical structures, particularly vessels and organs;
medical instruments and devices.

In a still further example of the method described herein,
the augmentation provided via the augmented reality device
includes multiple windows, wherein at least one of, particu-
larly each of the multiple windows shows a slice image
having a sectional plane that differs from the sectional
plane(s) of the one or more other slice images.

In a specific example, the AR-overlay includes three
different virtual screens, wherein a first virtual screen shows
a probe's-eye view and the two remaining virtual screens
show inline views which extend perpendicularly to each
other and have a sectional plane which may contain an
anatomical direction. For example, the sectional plane of a
first inline view may extend along a cranial-caudal direction,
whereas a second inline view may have an image plane
extending along a medial-lateral direction of the patient's
anatomy.

As was already indicated further above, the at least one
object of interest may be selected from the group compris-
ing:
permanent medical implants, particularly bone screws and
bone nails;
temporary medical implants, particularly electrodes and
catheters;
pathological anatomical structures, particularly tumors
and lesions;
treatment volumes, particularly radiation dose distribu-
tions, particle radiation fields and electromagnetic
radiation fields;
anatomical structures, particularly vessels and organs;
medical instruments and devices.

In as far as an object of interest remains static with respect
to the patient's anatomy, it's position and/or orientation with
respect to the patient's anatomy may be determined only
once, such that it's three-dimensional representation shown
in the AR-overlay remains invariant with respect to the
three-dimensional image dataset from which the two-dimen-
sional slice images are reconstructed. However, it is also
conceivable that at least one object of interest may change
it's position and/or orientation with respect to the patient's
actual anatomy and consequently also with respect to the
three-dimensional image dataset, such that its spatial posi-
tion and/or orientation needs to be monitored over time so as
to display its current position and/or orientation with respect
to the three-dimensional image dataset.

In a still further example of the method described herein,
the three-dimensional representation of the at least one
object of interest is fading with an increased distance from
the sectional plane of the at least one slice image, particu-
larly with an increased distance from a predefined clearance
from the sectional plane.

The three-dimensional representation of the at least one
object of interest can be visually set apart from the two-
dimensional slice image, for example by coloring the three-
dimensional representation while the slice images are shown
in grayscale. In order to avoid "cramming" the content of the
virtual screens, those parts of the three-dimensional repre-
sentations which reach beyond a predefined threshold dis-
tance from the plane of the virtual screens may not be shown
in the AR-overlay, for example by fading out these parts of
the three-dimensional representation. In a first example, the
threshold distance may be a distance from the screen plane
at the front and/or at the back of the screen, wherein the threshold distance at the front of the screen may even differ
from the threshold distance at the back of the screen. Either
one or both of those distances may be set to "O" such that
the three-dimensional representation begins to increasingly
fade with an increased distance from the screen plane. In a
second example, those parts of the three-dimensional rep-
resentation which reach beyond the threshold distance
defined for the front side and/or for the back side may even
be invisible, i.e. not shown in the augmentation. Thus, these
parts of the three-dimensional representation appear "cut
off" in the augmentation while the parts of the three-
dimensional representation within the threshold volume may
be shown without any fading. By doing so, the user receives
a mainly two-dimensional visualization, but still receives a
good perception about how objects of interest are positioned
and/or oriented with respect to the patient's anatomy and the
slice images. Further, showing the three-dimensional repre-
sentations only within a predefined threshold volume with
respect to the virtual screens avoids "cramming" the virtual
screens with image content. In still another example, a
three-dimensional representation of at least one object of
interest may be not shown in the augmentation, i.e. rendered
invisible for situations in which the respective object of
interest does not intersect with the sectional plane of the
slice image. This means that a three-dimensional represen-
tation of one or more objects of interest is not shown in case
the representation does not intersect with the plane of the
virtual screen or image representation shown in the aug-
mentation. As soon as the object of interest intersects with
the slice image's sectional plane, for example caused by
moving a movable object and/or the object of interest with
respect to the patient's anatomy, the three-dimensional rep-
resentation may appear in the augmentation, for example
over its entire extension, or with those parts reaching beyond
a predefined threshold distance being faded out or cut off.

In a further example of the method described herein may
include the steps of:
acquiring input data which describes at least one user
input, particularly a gesture performed by a user and
detected via a camera system;
determining, based on the augmentation data and the
input data, control data which describes a manipulation
of the augmentation of the field of view, particularly of
at least one of the location, orientation and size of the
augmentation within the field of view;
the content of the at least one slice image;
the three-dimensional representation of the at least one
object.

In other words, the method suggested herein provides the
possibility for a user to interact with the content shown in the
AR-overlay, particularly manipulating this content in a
desired manner.

In a second aspect, the invention is directed to a computer
program comprising instructions which, when the program
is executed by at least one computer, causes the at least one
computer to carry out method according to the first aspect.
The invention may alternatively or additionally relate to a
(physical, for example electrical, for example technically
generated) signal wave, for example a digital signal wave,
such as an electromagnetic carrier wave carrying informa-
tion which represents the program, for example the afore-
mentioned program, which for example comprises code
means which are adapted to perform any or all of the steps
of the method according to the first aspect. The signal wave
is in one example a data carrier signal carrying the afore-
mentioned computer program. A computer program stored
on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program, i.e. comprising the program.

In a third aspect, the invention is directed to a computer-readable storage medium on which the program according to the second aspect is stored. The program storage medium is for example non-transitory.

In a fourth aspect, the invention is directed to at least one computer (for example, a computer), comprising at least one processor (for example, a processor), wherein the program according to the second aspect is executed by the processor, or wherein the at least one computer comprises the computer-readable storage medium according to the third aspect.

In a fifth aspect, the invention is directed to a medical system, comprising:

a) the at least one computer according to the fourth aspect;

b) at least one electronic data storage device storing at least the three-dimensional image-dataset of the patient's anatomy and/or the spatial position and a three-dimensional model of the at least one object of interest;

c) a medical tracking system configured to determine the spatial position of the movable object; and d) an augmented reality device, particularly AR-goggles or AR-spectacles, configured to augment the field of view as seen through the augmented reality device with digital image content;

wherein the at least one computer is operably coupled to the at least one electronic data storage device for acquiring, from the at least one data storage device, the three-dimensional image dataset of the patient's anatomy and/or the spatial position and a three-dimensional model of the at least one object of interest;

the medical tracking system for acquiring, from the medical tracking system, the spatial position of the movable object;

the augmented reality device for issuing a control signal to the augmented reality device for controlling the operation of the augmented reality device on the basis of the augmentation data.

Alternatively or additionally, the invention according to the fifth aspect is directed to a for example non-transitory computer-readable program storage medium storing a program for causing the computer according to the fourth aspect to execute the data processing steps of the method according to the first aspect.

In an example of the system described herein, the at least one computer is included in the augmented reality device and is configured to reconstruct the at least one slice image from the three-dimensional image dataset received from the at least one electronic data storage device; and/or render the three-dimensional representation of the at least one object of interest from the model and the spatial position of at least one object of interest.

In other words, a major part of the processing (rendering) work is done by the at least one computer included in the augmented reality device, which may be referred to as client site rendering.

In a further example of the system described herein, the electronic data storage device is included in a transportable or stationary unit of a medical navigation system which is in particular operably coupled to the augmented reality device via a wireless data connection. In this context, the transportable or stationary unit of a medical navigation system may be referred to as server site, which for example may not provide computational (e.g. rendering) work in regards to the AR-overlay.

In a still further example of the device described herein, the augmented reality device is configured to block out at least one predefined section of the field of view, and wherein at least the field of view covered by the at least one slice image and/or a three-dimensional representation of the at least one object of interest is blocked out.

A further example of the system described herein includes a gesture detection unit configured to detect a gesture performed by a user, particularly within at least one camera image received by the medical tracking system, and to output control data corresponding to the gesture performed by the user for manipulation of the augmentation of the field of view.

According to a further example of the method and/or the system described herein, the augmentation further includes at least one three-dimensional representation of the patient's anatomy, particularly comprising a three-dimensional representation registered with the patient's actual anatomy within the field of view provided via the augmented reality device.

For example, the disclosed method is not a method for treatment of the human or animal body by surgery or therapy. For example, the invention does not involve or in particular comprise or encompass an invasive step which would represent a substantial physical interference with the body requiring professional medical expertise to be carried out and entailing a substantial health risk even when carried out with the required professional care and expertise.

Definitions

In this section, definitions for specific terminology used in this disclosure are offered which also form part of the present disclosure.

The method in accordance with the invention is for example a computer-implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II, III, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a computer program comprising instructions which, when on the program is executed by a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein. The signal wave is in one example a data carrier signal carrying the aforementioned computer program. The invention also relates to a computer comprising at least one processor and/or the aforementioned computer-readable storage medium and for example a memory, wherein the program is executed by the processor.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The n-dimensional image of a body is registered when the spatial location of each point of an actual object within a space, for example a body part in an operating theatre, is assigned an image data point of an image (CT, MR, etc.) stored in a navigation system.

Image registration is the process of transforming different sets of data into one coordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

A pointer is a rod which comprises one or more-advantageously, two-markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:

a computer for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
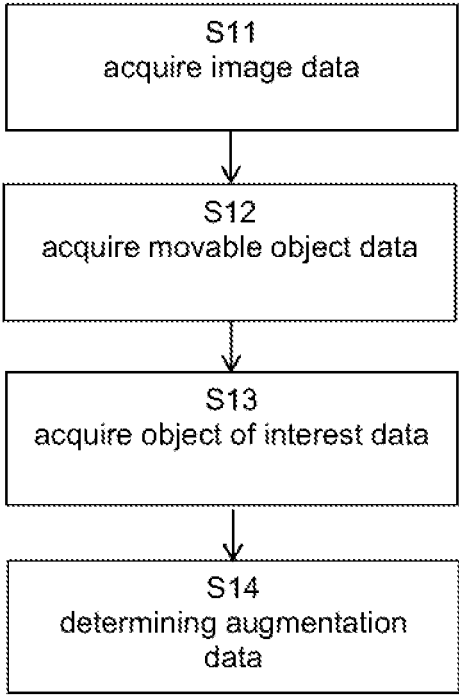
FIG. 1 illustrates the basic steps of the method according to the first aspect.

FIG. 1 illustrates the basic steps of the method according to the first aspect, in which step S11 encompasses acquiring image data, step S12 encompasses acquiring movable object data, step S13 encompasses acquiring object of interest data and subsequent step S14 encompasses determining augmentation data.

Figure 2:
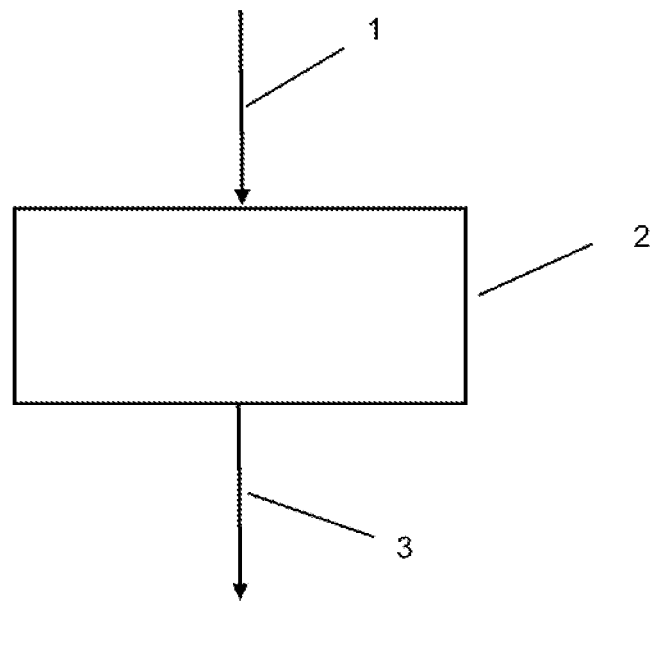
FIG. 2 shows an embodiment of the present invention, specifically the method according to the first aspect.

FIG. 2 illustrates an embodiment of the present invention that includes all essential features of the invention. In this embodiment, the entire data processing which is part of the method according to the first aspect is performed by a computer 2. Reference sign 1 denotes the input of data acquired by the method according to the first aspect into the computer 2 and reference sign 3 denotes the output of data determined by the method according to the first aspect.

Figure 3:
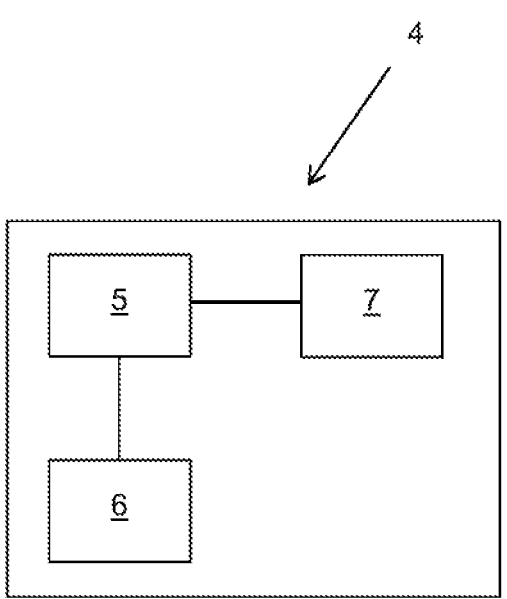
FIG. 3 is a schematic illustration of the system according to the fifth aspect.

FIG. 3 is a schematic illustration of the medical system 4 according to the fifth aspect. The system is in its entirety identified by reference sign 4 and comprises a computer 5, an electronic data storage device (such as a hard disc) 6 for storing at least the patient data and a medical device 7 (such as a radiation treatment apparatus). The components of the medical system 4 have the functionalities and properties explained above with regard to the fifth aspect of this disclosure.

Figure 4:
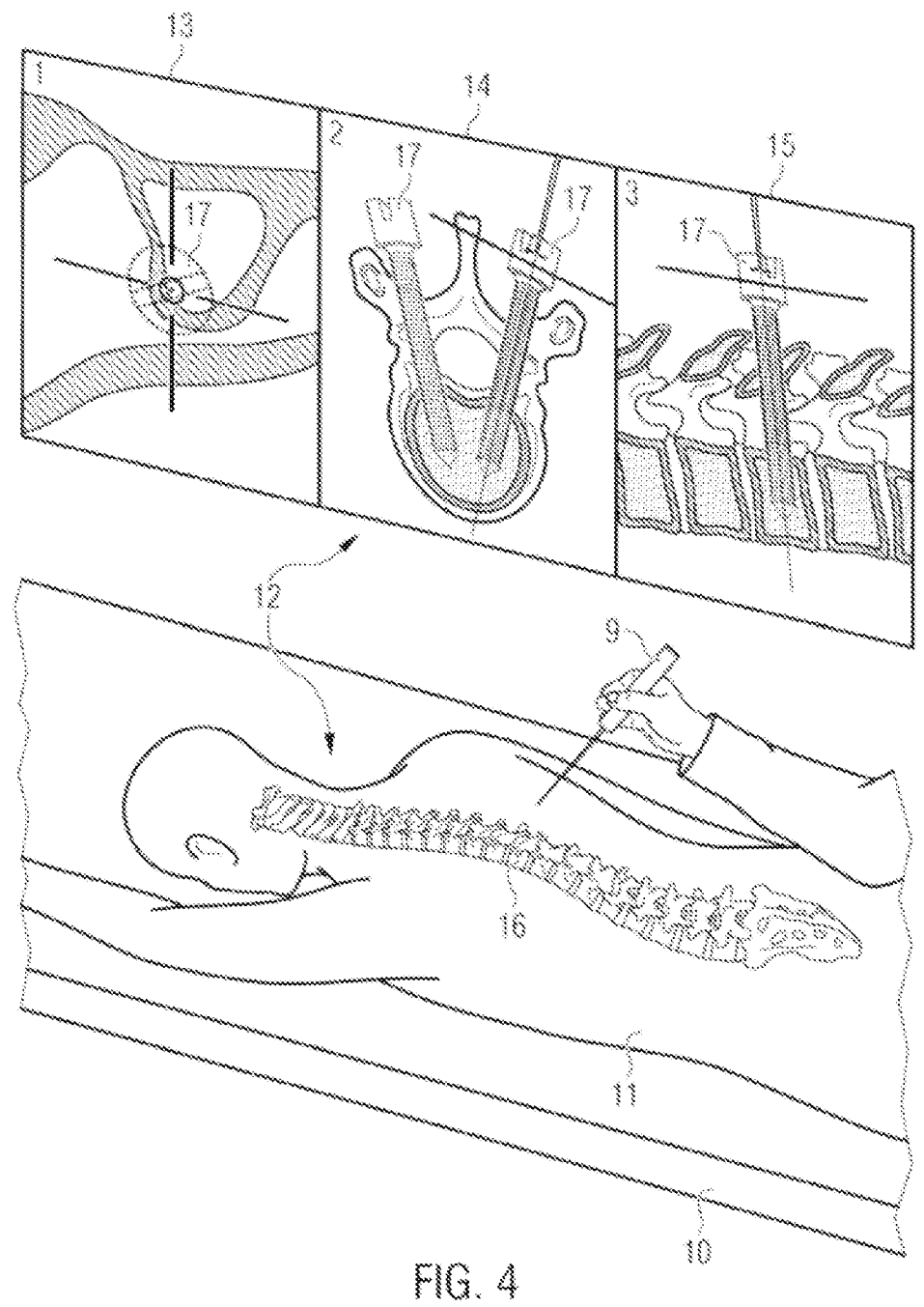
FIG. 4 shows a user's field of view.
Figure 7:
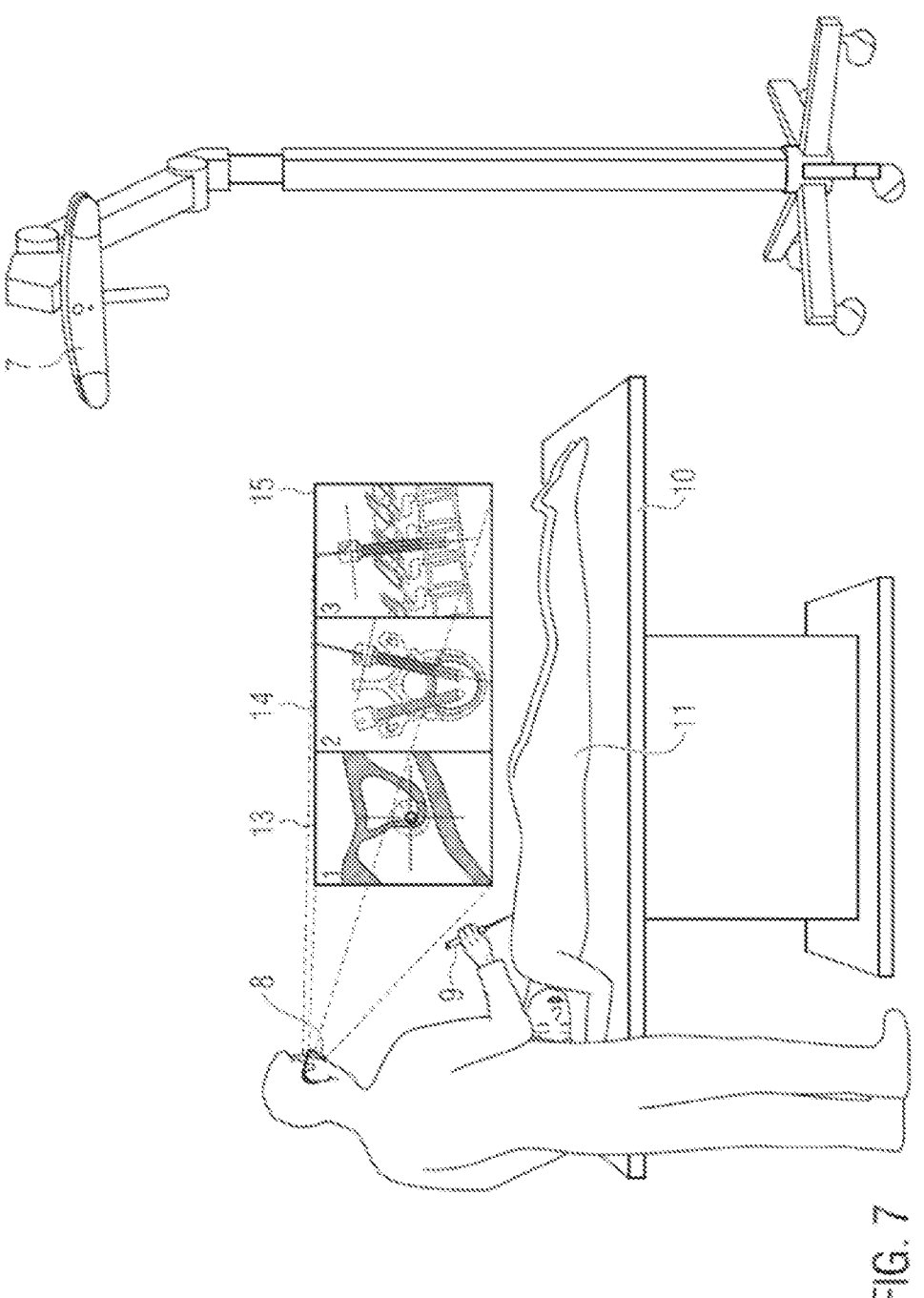
FIG. 7 shows a surgical site with a user wearing an AR-device according to the fifth aspect.

FIG. 4 shows a field of view of a user, which does not only include real-world objects such as a pointer instrument 9, a patient table 10 as well as a patient's anatomy 11. With the help of an AR-device 8 (c.f. FIG. 7), the user's field of view is augmented with a virtual overlay 12 including three virtual screens 13, 14, 15 as well as a three-dimensional representation of the patient's spine 16 representing a part of the patient's anatomy 11. Each one of the screens 13, 14, 15 shows a slice image of the patient's anatomy 11, which has been reconstructed from a previously acquired three-dimensional image dataset of the patient's anatomy 11. The respective sectional planes of the images shown on the virtual screens 13, 14, 15 are defined based on anatomical directions defined for the patient's anatomy 11, and the spatial position and/or orientation of the pointer instrument 9. Screen 13 shows a so-called probe's-eye view, the sectional plane of which extends perpendicularly to the longitudinal axis of pointer 9. Thus, screen 13 shows a view from above onto the patient's anatomy and along the longitudinal axis of pointer 9. Screen 14 shows a first inline view, wherein the sectional plane of the shown image is defined by the medial-lateral direction defined for the patient's anatomy 11, as well as by the longitudinal axis of pointer 9. Thus, screen 14 will always show a slice image including the longitudinal axis of pointer 9 and a medial-lateral direction defined for the patient's anatomy 11. In a similar manner, screen 15 shows a second slice image the sectional plane of which is defined by the longitudinal axis of pointer 9 and the cranial-caudal direction defined for the patient's anatomy 11.

Each one of the virtual screens 13, 14, 15 shows, in addition to the respective two-dimensional slice images, three-dimensional representations of pedicle screws already placed within the patient's spine 16.

By moving pointer 9 with respect to the patient's spine 16, the user is able to change the content shown on virtual screens 13, 14, 15 as the sectional planes of the slice images are changed corresponding to the motion of pointer 9.

The user's perception of the medical situation is improved as the field of view is not only augmented with a three-dimensional representation of the patient's spine 16 which is spatially aligned with the patient's actual anatomy 11, but also includes virtual screens 13, 14, 15 which show three-dimensional representations of pedicle screws 17 positionally aligned within the two-dimensional slice images shown on the respective screens 13, 14, 15.

Figure 5:
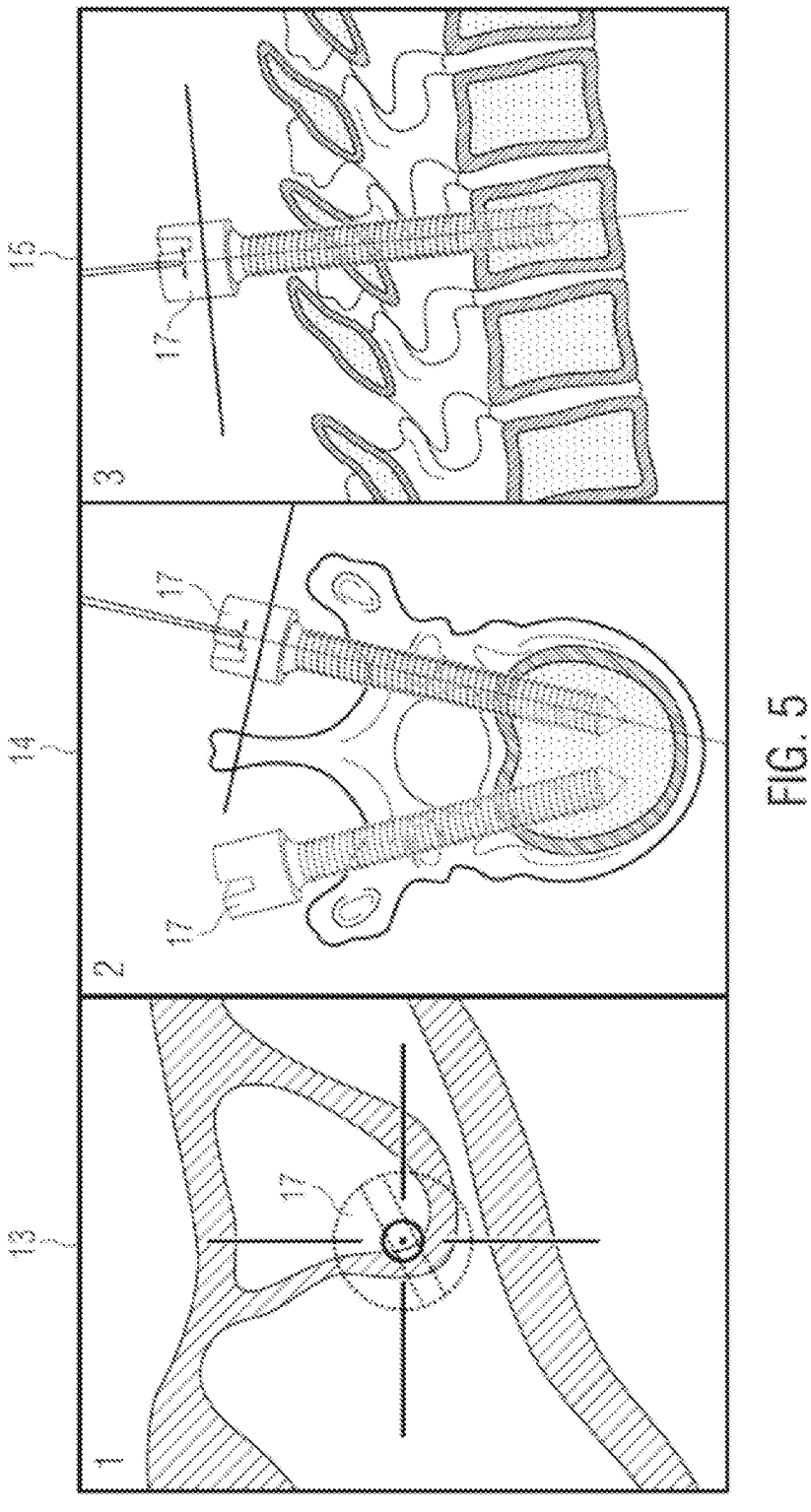
FIG. 5 shows three virtual screens as contained in the AR-overlay of FIG. 4.
Figure 6:
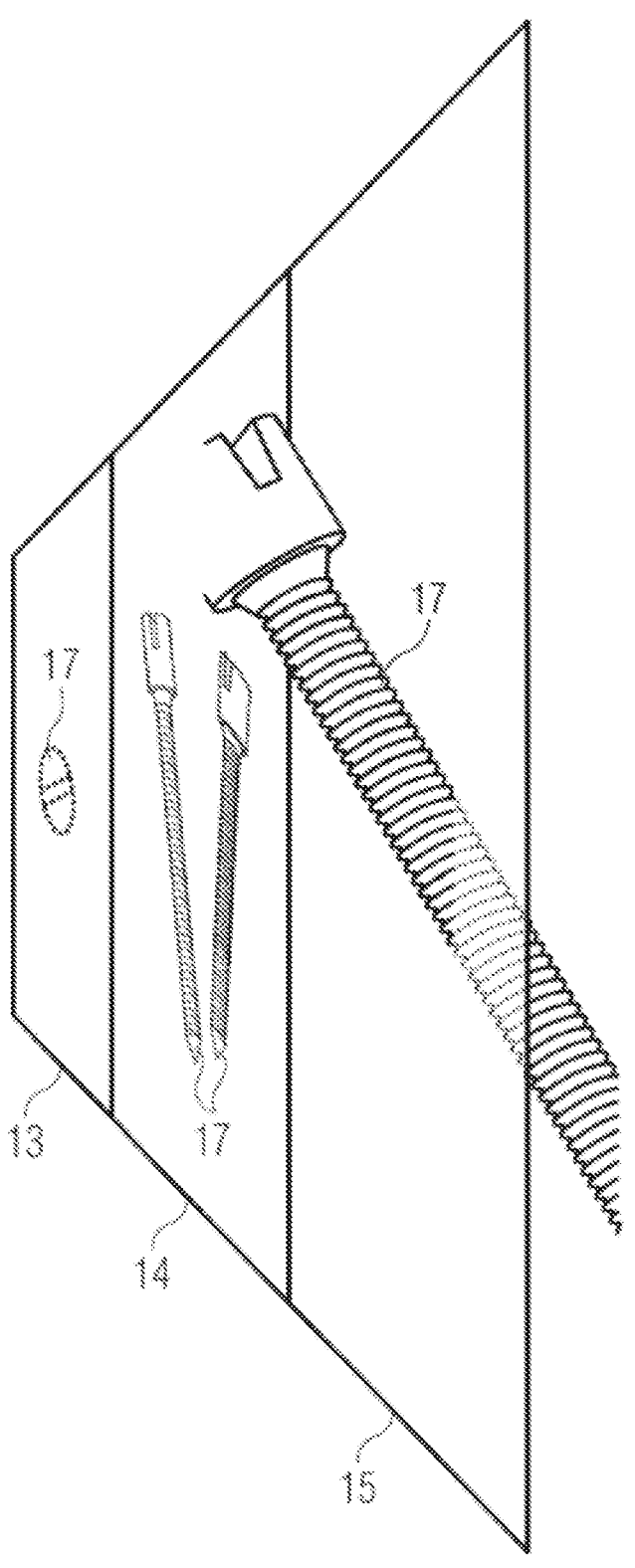
FIG. 6 shows the virtual screens of FIG. 5 as seen from an acute angle.

FIGS. 5 and 6 show a more detailed view on the three virtual screens 13, 14, 15 of FIG. 4. It becomes apparent therefrom that the two-dimensional screens 13, 14, 15 not only show two-dimensional slice images of the patient's anatomy 11, but also include three-dimensional representations of pedicle screws 17 which are shown in a correct positional alignment with the shown 2D-images of the patient's anatomy 11 (not shown in FIG. 6). It further becomes apparent that those parts of the three-dimensional representations of the pedicle screws 17 which reach beyond a threshold distance from the plane of screens 14 and 15 are not shown, but are rather "faded out"/"cut off".

FIG. 7 shows a surgical site with a patient 11 lying in a prone position on a patient table 9. A surgeon wearing AR-spectacles 8 is holding a pointer instrument 9 the position of which is tracked via tracking system 7. Based on the determined position of pointer 9 with respect to the patient's anatomy 11, AR-spectacles 8 provide an overlay including three virtual screens 13, 14, 15 each of which showing a two-dimensional anatomical slice view of the patient's anatomy 11 along with three-dimensional representations of pedicle screws 17.

The invention claimed is:

1. A computer-implemented method of providing an augmentation of a field of view via an augmented reality device comprising:

acquiring image data which describes at least one slice image of a patient's anatomy reconstructed from a three-dimensional image dataset registered with the patient's actual anatomy;

acquiring movable object data which describes a spatial position of a movable object, particularly a handheld device or instrument, with respect to the patient's actual anatomy;

acquiring object of interest data which describes a model and a spatial position of at least one object of interest with respect to the three-dimensional image dataset;

determining, based on the image data, the movable object data and the object of interest data, augmentation data which describes the augmentation of the field of view provided via the augmented reality device, including the at least one slice image and a three-dimensional visual representation of the at least one object of interest positionally aligned with the at least one slice image in a merged visualization; and wherein a sectional plane of the at least one slice image is defined based on the spatial position of the movable object.

2. The method according to claim 1, wherein the at least one slice image of the patient's anatomy includes:

at least one two-dimensional image of the patient's anatomy; or at least one planar, three-dimensional image volume having a limited slice-thickness, with the sectional plane forming the centre plane of the image volume.

3. The method according to claim 1, wherein the sectional plane of the at least one slice image is defined:

to include a longitudinal axis of the movable object; or to extend perpendicularly with respect to the longitudinal axis of the movable object.

4. The method according to claim 1, wherein the sectional plane of the at least one slice image is defined to extend in an anatomical direction defined for the patient's anatomy, in:

a cranial-caudal direction;

a medial-lateral direction; or an anterior-posterior direction.

5. The method according to claim 1, the at least one object of interest being at least one of:

permanent medical implants, particularly bone screws and bone nails;

temporary medical implants, particularly electrodes and catheters;

pathological anatomical structures, particularly tumors and lesions;

treatment volumes, particularly radiation dose distributions, particle radiation fields and electromagnetic radiation fields;

anatomical structures, particularly vessels and organs; and medical instruments and devices.

6. The method according to claim 1, wherein the augmentation provided via the augmented reality device includes multiple windows, wherein at least one of the multiple windows shows a slice image having a sectional plane that differs from the sectional plane(s) of the one or more other slice images.

7. The method according to claim 1, wherein the three-dimensional representation of the at least one object of interest is:

fading with an increased distance from the sectional plane of the at least one slice image, with an increased distance from a predefined clearance from the sectional plane; or not displayed in the augmentation in case the at least one respective object of interest does not intersect with the sectional plane.

8. The method according to claim 1, further including the steps of:

acquiring input data which describes at least one user input of a gesture performed by a user and detected via a camera system; and determining, based on the augmentation data and the input data, control data-which describes a manipulation of the augmentation of the field of view of:

at least one of the location, orientation and size of the augmentation within the field of view;

the content of the at least one slice image; and the three-dimensional representation of the at least one object of interest.

9. A non-transitory computer readable medium comprising instructions which, when executed by a computer, cause the computer to:

acquire image data which describes at least one slice image of a patient's anatomy reconstructed from a three-dimensional image dataset registered with the patient's actual anatomy;

acquire movable object data which describes a spatial position of a movable object, particularly a handheld device or instrument, with respect to the patient's actual anatomy;

acquire object of interest data which describes a model and a spatial position of at least one object of interest with respect to the three-dimensional image dataset;

determine, based on the image data, the movable object data and the object of interest data, augmentation data which describes the augmentation of a field of view provided via an augmented reality device, including the at least one slice image and a three-dimensional visual representation of the at least one object of interest positionally aligned with the at least one slice image in a merged visualization, wherein a sectional plane of the at least one slice image is defined based on the spatial position of the movable object.

10. A medical system for providing an augmentation of a field of view via an augmented reality device, comprising:

at least one processor executing instructions causing the at least one processor to:

acquire image data which describes at least one slice image of a patient's anatomy reconstructed from a three-dimensional image dataset registered with the patient's actual anatomy;

acquire movable object data which describes a spatial position of a movable object, particularly a handheld device or instrument, with respect to the patient's actual anatomy;

acquire object of interest data which describes a model and a spatial position of at least one object of interest with respect to the three-dimensional image dataset;

determine, based on the image data, the movable object data and the object of interest data, augmentation data which describes the augmentation of the field of view provided via the augmented reality device, including the at least one slice image and a three-dimensional visual representation of the at least one object of interest positionally aligned with the at least one slice image in a merged visualization, wherein a sectional plane of the at least one slice image is defined based on the spatial position of the movable object;

at least one electronic data storage device storing the three-dimensional image dataset of the patient's anatomy or the spatial position and a three-dimensional model of the at least one object of interest;

a medical tracking system configured to determine the spatial position of the movable object; and an augmented reality device, configured to augment the field of view as seen through the augmented reality device with digital image content;

wherein the at least one processor is operably coupled to:

the at least one electronic data storage device for acquiring, from the at least one data storage device, the three-dimensional image dataset of the patient's anatomy or the spatial position and a three-dimensional model of the at least one object of interest;

the medical tracking system for acquiring, from the medical tracking system, the spatial position of the movable object; and the augmented reality device for issuing a control signal to the augmented reality device for controlling the operation of the augmented reality device on the basis of the augmentation data.

11. The medical system of claim 10, wherein the at least one processor is included in the augmented reality device and is configured to:

render the three-dimensional representation of the at least one object of interest from the model and the spatial position of at least one object of interest.

12. The medical system of claim 10, wherein the electronic data storage device is included in a medical navigation system which is operably coupled to the augmented reality device via a wireless data connection.

13. The medical system of claim 10, wherein the augmented reality device is configured to block out at least one predefined section of the field of view, and wherein at least the field of view covered by the at least one slice image and a three-dimensional representation of the at least one object of interest is blocked out.

14. The medical system of claim 10, further including a gesture detection unit configured to detect a gesture performed by a user, within at least one camera image received by the medical tracking system, and to output control data corresponding to the gesture performed by the user for manipulation of the augmentation of the field of view.

15. The medical system of claim 10, wherein the augmentation further includes at least one three-dimensional representation of the patient's anatomy, comprising a three-dimensional representation registered with the patient's actual anatomy within the field of view provided via the augmented reality device.

* * * * *